(12) United States Patent
Yan et al.

(10) Patent No.: US 12,104,190 B2
(45) Date of Patent: Oct. 1, 2024

(54) TAXADIENE SYNTHASE TcTS2, ENCODING NUCLEOTIDE SEQUENCE AND USE THEREOF

(71) Applicant: AGRICULTURAL GENOMICS INSTITUTE AT SHENZHEN, CHINESE ACADEMY OF AGRICULTURAL SCIENCES, Shenzhen (CN)

(72) Inventors: Jianbin Yan, Shenzhen (CN); Junbo Gou, Shenzhen (CN); Qinggang Liao, Shenzhen (CN); Haifei Liang, Shenzhen (CN); Chong Li, Shenzhen (CN); Ran Du, Shenzhen (CN); Xingyao Xiong, Shenzhen (CN); Sanwen Huang, Shenzhen (CN)

(73) Assignee: Agricultural Genomics Institute at Shenzhen, Chinese Academy of Agricultural Sciences, Shenzhen (CN)

( * ) Notice: Subject to any disclaimer, the term of this patent is extended or adjusted under 35 U.S.C. 154(b) by 0 days.

(21) Appl. No.: 18/147,862

(22) Filed: Dec. 29, 2022

(65) Prior Publication Data

US 2023/0220369 A1   Jul. 13, 2023

Related U.S. Application Data

(63) Continuation of application No. PCT/CN2021/097561, filed on Jun. 1, 2021.

(30) Foreign Application Priority Data

Jul. 7, 2020 (CN) .......................... 202010647327.3

(51) Int. Cl.
   *C12N 9/88*     (2006.01)
   *C12N 15/52*    (2006.01)
   *C12N 15/82*    (2006.01)

(52) U.S. Cl.
   CPC .............. *C12N 9/88* (2013.01); *C12N 15/52* (2013.01); *C12N 15/8243* (2013.01); *C12Y 402/03017* (2013.01)

(58) Field of Classification Search
   None
   See application file for complete search history.

(56) References Cited

U.S. PATENT DOCUMENTS

2010/0297722 A1   11/2010  Anterola et al.

FOREIGN PATENT DOCUMENTS

| CN | 1560255 A | 1/2005 |
| CN | 101001947 A | 7/2007 |
| CN | 102643843 A | 8/2012 |
| CN | 102812129 A | 12/2012 |
| CN | 107674881 A | 2/2018 |
| CN | 110904148 A | 3/2020 |
| CN | 111748547 A | 10/2020 |
| IN | 102643839 A | 8/2012 |
| WO | 2005080579 A2 | 9/2005 |
| WO | 2007081772 A2 | 7/2007 |

OTHER PUBLICATIONS

Guo et al. Proceedings of the National Academy of Sciences 101.25 (2004): 9205-9210. (Year: 2004).*
McElroy et al. Biotechnology of natural products (2018): 145-185 (Year: 2018).*
Syklowska-Baranek et al. Plant Cell, Tissue and Organ Culture (PCTOC) 120 (2015): 1051-1059. (Year: 2015).*
GenBank: AY424738.1—Taxus baccata taxadiene synthase (TXS) mRNA, complete cds https://www.ncbi.nlm.nih.gov/nuccore/AY424738 (Year: 2003).*
Köksal et al. Nature 469.7328 (2011): 116-120 (Year: 2011).*
Xiong et al. Nature Plants 7.8 (2021): 1026-1036. (Year: 2021).*
Rivera et al. Physics of life reviews 9.3 (2012): 308-345. (Year: 2012).*
Xiong Xingyao, et al.; The Taxus genome provides insights into paclitaxel biosynthesis; BIORXIV; Apr. 29, 2021; pp. 1-44; USA.
Long, R.M, et al.; Synthetic construct taxa-4(5), 11(12)-diene synthase mRNA, complete cds; GenBank: Ay364470.1; Jan. 9, 2004; Online.
CNIPA First Office Action for Application CN202010647327.3, issued Feb. 18, 2021.
PCT International Search Report for PCT/CN2021/097561, mailed Aug. 27, 2021.
PCT Written Opinion for PCT/CN2021/097561, mailed Aug. 27, 2021.

* cited by examiner

*Primary Examiner* — Anne Kubelik
(74) *Attorney, Agent, or Firm* — Flener IP & Business Law; Zareefa B. Flener

(57) ABSTRACT

Provided are a taxadiene synthase TcTS2, an encoding nucleotide sequence and use thereof. The amino acid sequence of TcTS2 includes or consists of: (a) an amino acid sequence represented by SEQ ID NO: 1; or (b) a functional homologous sequence having at least 80% sequence similarity with the amino acid sequence represented by SEQ ID NO: 1; or (c) an amino acid sequence having TcTS2 activity with addition, deletion, or substitution of one or more amino acids in the amino acid sequence represented by SEQ ID NO: 1. TcTS2 and the nucleotide sequence encoding the TcTS2 provide new gene resources for improving the yield of taxol, and they may be used for modifying chassis hosts by plant genetic engineering and metabolic engineering strategies to produce taxol and the intermediates thereof etc., thereby having significant economic and social value.

17 Claims, 3 Drawing Sheets
Specification includes a Sequence Listing.

SEQUENCE LISTING

```
Sequence total quantity: 14
SEQ ID NO: 1            moltype = AA  length = 758
FEATURE                 Location/Qualifiers
source                  1..758
                        mol_type = protein
                        note = Amino acid sequence of Taxadiene Synthase TcTS2
                        organism = unidentified
SEQUENCE: 1
MSSSPTKLAT ENANAVAESN LIPRLSANYH GDLWHHGVIQ TLQTPYQESS SYQERAEELI   60
VKIKDMFKAV EEGAISPSAY DTAWVARVPD GSEKPRFPQA LNWLLHNQLQ DGSWGLESHF  120
MLSDRLLSTL NSVISLLVWK TGQQQVEQGT LFITENLKLL EGEDELPPDF EIIFPALLQK  180
AKALGMSLPD HDLPFIKSLS VAREARLASY TDNNIPASML NALEGLEEVI DWDKIMRFQM  240
PCLYSIDLLE RLSLVDNIEH LGIGRHFKQE IKVALDYVYR YWSERGIGLG RDSLIPDLNT  300
TALGLRTLRA HGYNVSSEVL NNFKDENGRF FSSLGQTHVE LRSMVNLLRA SDLAFPDEPL  360
MDDAKIFAEA YLRDALATRI STNTKLFKEI DYAVEYPWHM SIPRLEARSY IDVYDDDYTW  420
QNKTLYRMSN LSNAYCLELA KLDFNIVQSL HQEELKLLTR WWKESGMADI NFTRHRVAEV  480
YFSSATFEPE YSSTRIAFTK IGCLQVLFDD MADIFATLDE LRDFTEGVKR WDTSLIHKLP  540
DCMQTCFRVW FNLMEEVNND VSNVQGRDML NHIRKPWELY FNCYVQEREW LDAGYIPTLE  600
EYLKTYSISV GLGPCTLQPI LLMGDIVKDD VVEKVHYPSN LFELVSLSWR LTNDTKTYQA  660
EKARGQQASG IACYMKDNPG STEEDAIKYI CGVVDRALKE ACFEYFKPAD DVPMSCKSFI  720
FNLRLCVQIF YKFIDGYGIA NEEIKDYIRK VYIEPIQV                         758

SEQ ID NO: 2            moltype = AA  length = 815
FEATURE                 Location/Qualifiers
source                  1..815
                        mol_type = protein
                        note = Amino acid sequence of Taxadiene Synthase TcTS2
                        organism = unidentified
SEQUENCE: 2
MAQLSFNSAV KMNANANAWC GNKAIHGPTN HRVKSEGRRK MWFCSKAAGT RYCPVLMMSS   60
SPTKLATENA NAVAESNLIP RLSANYHGDL WHHGVIQTLQ TPYQESSSYQ ERAEELIVKI  120
KDMFKAVEEG AISPSAYDTA WVARVPDGSE KPRFPQALNW LLHNQLQDGS WGLESHFMLS  180
DRLLSTLNSV ISLLVWKTGQ QQVEQGTLFI TENLKLLEGE DELPPDFEII FPALLQKAKA  240
LGMSLPDHDL PFIKSLSVAR EARLASYTDN NIPASMLNAL EGLEEVIDWD KIMRFQMPCL  300
YSIDLLERLS LVDNIEHLGI GRHFKQEIKV ALDYVYRYWS ERGIGLGRDS LIPDLNTTAL  360
GLRTLRAHGY NVSSEVLNNF KDENGRFFSS LGQTHVELRS MVNLLRASDL AFPDEPLMDD  420
AKIFAEAYLR DALATRISTN TKLFKEIDYA VEYPWHMSIP RLEARSYIDV YDDDYTWQNK  480
TLYRMSNLSN AYCLELAKLD FNIVQSLHQE ELKLLTRWWK ESGMADINFT RHRVAEVYFS  540
SATFEPEYSS TRIAFTKIGC LQVLFDDMAD IFATLDELRD FTEGVKRWDT SLIHKLPDCM  600
QTCFRVWFNL MEEVNNDVSN VQGRDMLNHI RKPWELYFNC YVQEREWLDA GYIPTLEEYL  660
KTYSISVGLG PCTLQPILLM GDIVKDDVVE KVHYPSNLFE LVSLSWRLTN DTKTYQAEKA  720
RGQQASGIAC YMKDNPGSTE EDAIKYICGV VDRALKEACF EYFKPADDVP MSCKSFIFNL  780
RLCVQIFYKF IDGYGIANEE IKDYIRKVYI EPIQV                            815

SEQ ID NO: 3            moltype = DNA  length = 5138
FEATURE                 Location/Qualifiers
source                  1..5138
                        mol_type = other DNA
                        note = Nucleotide sequence coding Taxadiene Synthase TcTS2
                        organism = unidentified
SEQUENCE: 3
attccatgtg gctttgatca tgataatgga ttggtgtcct acaaggcaca ttaattaggt   60
aagatccttt atatcaacgt ataacataat cccttcacaa ttagatgtac gttgatatca  120
tcgtataaca ttaataggtc gatgggtggg aatagagatt aacatggagt caacgaaaac  180
cttcacttgg tgatgttgaa aactacatta tccattacaa aaaggctttt tagattatat  240
aaatttaata gtcattgatt gtttgcatcg atgattacta tctatgtttg taaatgacaa  300
tcaaatatat atcaaattta atactgaaat tgcataacga gaatcagatg atgttaatgt  360
aactacacta atgcgtaaaa ttcgggaaaa aaaaatagtg agaaagaaaa agtgttaaac  420
tccattctat gacaaagata ctatgagagg aggaggcaaa aagtgtagaa gactaagcat  480
agaccaaaaa gaacaaaaac gaagactaag tagtacaaaa aacaaaagtg cctacttaaa  540
tgagaaaagc attgataaaa atagtaggta gattgtttgg gtttatacga ttaaaatatt  600
tatgggaaat tataatatgt aataaacaaa gcatattttg ttgcttacaa acatgatgtt  660
tttgacacat gcaatgcgga attttatttt agtaatttc cctgacagtt ttctctggct   720
```

```
tgagactttc tgacatgaga caagctttta gaaaatttag attaatatct atgtttgtaa    780
attgcaatca aatatatata tcaaatttaa tactgaaatt gtacaacgaa aatcagatga    840
ctacattaat gcggaaaaaa tatttagcga gaaagaaaga gtgttaaaact ccattctatg   900
acgaagatac tatgaaagga ggaggaggag aaaaacaaaa agaagatact atgaaaggag    960
gaggagaaaa acaaaagcgc ctacttaaat gagataagga ttgataaaaa tttgggttta  1020
tacgattaaa atatctaagg gtgattataa tatgtaataa aaacaagcgt aggtattttg   1080
ttgcttacaa acgtgatgtt tcggaattga aagaaatgtg agcgggcaaa tgcaaatgga  1140
gttggagttg gaattggcgc ttgcaaatta acatgtgat gagtgcctgc cgcctttgta   1200
tgctcatctc agtgaccccc tatttattta aactagctat tctgcaggac agtagacaag  1260
cattgaatct tagttttagt ttaaccaggt gatttggaat ctggaattcc cctgcagaaa  1320
atggctcagc tctcgtttaa ctcggcggtg aagatgaatg cgaatgcgaa tgcgaatgcg  1380
tggtgcggga acaaggcaat ccacggtcca acaaatcaca gagtaaaaag tgagggcagg  1440
agaaagatgt ggttttgctc caaggcagca gggacaaggt actgtcctgt cctaatgatg  1500
agcggtagcc cgaccaagtt ggctacgagc aatgccaatg cagttgcaga atctaattg   1560
atccctcgac tctccgccaa ttatcatggc gatctgtggc accatggcgt aatacaaaca  1620
ttacaaaaac cttaccaaga ggtaagccaa acaaaatttg taggtacatg tagggacatt  1680
gatttgtttt cttggctcac atttctgtca actgcagagt tcttcctacc aagaacgggc  1740
agaggagctt attgtgaaaa ttaaagatat gttcaaggca gttgaagagg gagcaataag  1800
tccatccgca tacgcactg cctgggtcgc aagggtgcct gatggatctg agaagccacg   1860
gtttccccag gccctcaact ggcttctaca caaccagctc caagatggat catgggtct   1920
tgaatcgcac tttatgctga gcgatcgatt gcttagcaca ctcaattctg ttatctcccc  1980
ccttgtttgg aaaacagggc agcagcaagt agaacaaggt gagaaatttt agctgtcctc  2040
atacatactc tgtaagaata gcattgcatt tagctgtcct catacataca ctgtttgttc  2100
aatcatataa ttttcttctc tacaggtact ttgtttatta cagagaatct aaaattactg  2160
gagggggaag atgagttgcc cccggacttt gaaataatct ttcctgctct gttgcaaaag  2220
gcaaaagcgc tgggaatgag tcttcctgat catgatcttc cattcatcaa atcttttgtcg 2280
gtagcacggg aagcgaggct tgcaagttac acagagtgag tgaaaacaga gctctataac  2340
tttggtgtgt gtttttggac attaatcaat cccaatgtac ttatggatta tgtgttttg   2400
gcattgcagc aacaatattc cagccagcat gttgaatgcg ttggagggtc tggaggaagt  2460
tattgattgg gacaagatta tgaggtttca aagtaaggat ggatcttttcc tgagctcccc 2520
tgcttccact gcatgtgtac tgatgcatac aggggacgaa agctgttttg ccttctcaa   2580
caatgtgctg gacaaattcg gcggctgcgg taataataat aataataata ataatgctac  2640
ttcttcccct ttaagtaatt aatttagtga agctgagaat gcattcaatg aaaactaact  2700
gtgtgaatta cagtgccctg tttgtattca atcgatctgc ttgaacgcct ttcgctggtt  2760
gacaacatcg agcatctcgg aatcggtcga catttcaaac aagaaatcaa ggtagctctt  2820
gattatgtct acaggtaacc taaccactcc attttgctat tctttttcc cttaccctgc   2880
cttttctttt cttgcaactg caccagtagc atcctaatta tatatata tggacagata    2940
ttggagtgaa agaggcatcg gtttgggtag agacagccta attcctgatc tgaacactac  3000
agccctcggc ctccgaaccc ttcgggccca tggatacaat gtttcctcgg gttagatact  3060
tacctgcctt taatcctatt attattattt caacataacg ttactgtcgc atttctttct  3120
ttatgctcat gatgtggaaa caaatactta tgaacgaacg cagaggtttt gaataatttc  3180
aaagatgaaa acgggcgctt cttctcctct cttggcaaaa cacatgtaga attgagaagc  3240
atggtgaacc ttttgagagc ttccgacctc gcatttcccg acgaaccact tatggacgat  3300
gctaaaatct ttgcagaagc atatcttaga gacgcacttg caacacgcat ctcaaccaat  3360
acaaaattat tcaagaggt tagtgctacc ttatttcccc ctttaaaatc cacatcacta   3420
atcctaccca aacccaaatt ttgttccttt ctctaatatc ataatcattt catttcgat   3480
cgactacgcg gtagagtacc cttggcacat gagtatccca cgtctcgagg cgagaagtta  3540
tattgatgta tacgacgatg attatacatg gcaaaataag actctataca ggtgggtcta  3600
aatatatgat cacatgagcc aagtaaattt tatacaaatt ccacgagcct tgttgcacta  3660
gttattatct ttctttaata ataaagttac aatctgtgca acagaatgtc aaacttgagt  3720
aacgcatatt gcttagaatt ggcgaaattg gacttcaatc ttgtgcaatc tttgcatcaa  3780
gaggagttga agcttctaac aaggtgggtc ataaattact gtgcattctc aacttatctt  3840
ataatttatc caaagataac acatttgtac taataatcta ctaacattat gggttttat   3900
gtcataagat ggtggaaaga atctggcatg gcagatataa acttcactcg acaccgagtg  3960
gcagaggtgt attttttcatc agctacgttt gaacccgaat attcttctac cagaatcgcc  4020
ttcaccaaaa ttggttgttt gcaagtcctg tttgacgaca tggccgacat ctttgcaaca  4080
ctagatgagt tgagagattt caccgaggga gtaaagaggt gattcatcaa aacttttaat  4140
ttgttttaat atttacaaat caaagccatg tcctaaaata catacataat ctgctagcgt  4200
aattgaacgt tttcgtaaat ttcagtaggg acacctcttt gatacacaag ctaccagact  4260
gtatgcaaac ttgctttaga gtttggttta acttaatgga agaagtcaat aacgacgtgt  4320
caaacgtaca aggccgtgac atgctcaatc acataagaaa acccgtaagt aattcaaatt  4380
gtagatgcca ccaaatccaa aaaaaatcgt agtatagatg gatttctttt ctacatgcct  4440
cataaacatt ggtactcaca tttaaacatt gttgtgtgac tcgaaatata gtgggagttg  4500
tacttcaatt gttatgtaca agaaagagag tggctcctga ctgggtatat accgactcta  4560
gaggagtacc taaagaccta ttctatatca gtaggccttg gaccatgtac tctacaacca  4620
atactactaa tgggcgatat cgtgaaagat gatgttgtcg agaaagtgca ctatccctca  4680
aatctatttg aacttgtatc cttgagctgg cgattaacaa atgacacaaa aacatatcag  4740
gtgcttcttg aatctcaaag tttcttctat atatacaaac ttgccactaa atgtgtacaa  4800
ccgcatgcta accttatttg tgtttcttcc ttggtgaagg tcgagaaggc tcgaggacaa  4860
caagcctcag gcatagcgtg ttatatgaag gataatccag gatcgacaga ggaagatgcc  4920
atcaagtaca tatgcggagt tgttgatcga gccttgaaag aggcatgctt tgaatatttc  4980
aagccagccg atgatgtccc aatgagttgc aagtcctta ttttcaacct cagactgtgt   5040
gtccaaatat tttacaagtt tatagatggg tatgaattg ccaacgagga gattaaggat   5100
tatataagaa aagtttacat tgaaccgatt caagtatg                          5138
```

SEQ ID NO: 4        moltype = DNA   length = 2448
FEATURE             Location/Qualifiers
source              1..2448
                    mol_type = other DNA

```
                        note = cDNA sequence coding Taxadiene Synthase TcTS2
                        organism = unidentified
SEQUENCE: 4
atggctcagc tctcgtttaa ctcggcggtg aagatgaatg cgaatgcgaa tgcgtggtgc    60
gggaacaagg caatccacgg tccaacaaat cacagagtaa aaagtgaggg caggagaaag   120
atgtggtttt gctccaaggc agcagggaca aggtactgtc ctgtcctaat gatgagcagt   180
agcccgacca agttgctac ggagaatgcc aatgcagttg cagaatctaa tttgatccct    240
cgactctccg ccaattatca tggcgatctg tggcaccatg gcgtaataca aacattacaa   300
acaccttacc aagagagttc ttcctaccaa gaacgggcag aggagcttat tgtgaaaatt   360
aaagatatgt tcaaggcagt tgaagaggga gcaataagtc catccgcata cgacactgcc   420
tgggtcgcaa gggtgcctga tggatctgag aagccacggt ttccccaggc cctcaactgg   480
cttctacaca accagctcca agatggatca tggggtcttg aatcgcactt tatgctgagc   540
gatcgattgc ttagcacact caattctgtt atctccctcc ttgtttggaa aacagggcag   600
cagcaagtag aacaaggtac tttgtttatt acagagaatc taaaattact ggaggggaa    660
gatgagttgc ccccggactt tgaaataatc tttcctgctc tgttgcaaaa ggcaaaagcg   720
ctgggaatga gtcttcctga tcatgatctt ccattcatca aatctttgtc ggtagcacgg   780
gaagcgaggc ttgcaagtta cacagacaac aatattccag ccagcatgtt gaatgcgttg   840
gagggtctgg aggaagttat tgattgggac aagattatga ggtttcaaat gccctgtttg   900
tattcaatcg atctgcttga acgccttttcg ctggttgaca catcgagca tctcggaatc   960
ggtcgacatt tcaaacaaga aatcaaggta gctcttgatt atgtctacag atattggagt  1020
gaaagaggca tcggtttggg tagagacagc ctaattcctg atctgaacac tacagccctc  1080
ggcctccgaa ccctcggc ccatggatac aatgtttcct cggaggtttt gaataatttc   1140
aaagatgaaa acgggcgctt cttctcctct cttggccaaa cacatgtaga attgagaagc   1200
atggtgaacc ttttgagagc ttccgacctc gcatttcccg acgaaccact tatggacgat  1260
gccaaaatct ttgcagaagc atatcttaga acgcacttg caacacgcat ctcaaccaat  1320
acaaaattat tcaaagagat cgactacgcg gtagagtacc cttggcaatg gagtatccca  1380
cgtctcgagg cgagaagtta tattgatgta tacgacgatg attatacatg caaaataag  1440
actctataca gaatgtcaaa cttgagtaac gcatattgct tagaattggc gaaattggac  1500
ttcaatattg tgcaatcttt gcatcaagag gagttgaagc ttctaacaag atggtggaaa  1560
gaatctggca tggcagatat aaacttcact cgacaccgaa tggcagaggt gtattttca   1620
tcagctacgt ttgaacccga atattcttct accagaatcg ccttcaccaa aattggttgt  1680
ttgcaagtcc tgtttgacga catggccgac atctttgcaa cactagatga gttgagagat  1740
ttcaccgagg gagtaaagag atgggacacc tctttgatac acaagctacc agactgtatg  1800
caaacttgct ttagagtttg gttaacttta atggaaacga cgtgtcaaac              1860
gtacaaggcc gtgacatgct caatcacata agaaaaccct gggagttgta cttcaattgg  1920
tatgtacaag aaagagagtg gctcgatgct gggtatatac cgactctaga ggagtaccta  1980
aagacctatt ctatatcagt aggccttgga ccatgtactc tacaaccaat actactaatg  2040
ggcgatatcg tgaaagatga tgttgtcgag aaagtgcact atcccatcaa tctatttgaa  2100
cttgtatcct tgagctggcg attaacaaat gacacaaaa catatcaggc tgagaaggct  2160
cgaggacaac aagcctcagg catagcgtgt tatatgaagg ataatccagg atcgacagag  2220
gaagatgcca tcaagtacat atgcggagtt gttgatcgag ccttgaaaga ggcatgcttt  2280
gaatatttca agcccagccga tgatgtccca atgagttgca agtcctttat tttcaacctc  2340
agactgtgtg tccaaatatt ttacaagttt atagatgggt atggaattgc caacgaggag  2400
attaaggatt atataagaaa agtttacatt gaaccgattc aagtatga              2448

SEQ ID NO: 5           moltype = DNA   length = 20
FEATURE                Location/Qualifiers
source                 1..20
                       mol_type = other DNA
                       note = Upstream primer for amplifying Taxadiene Synthase
                         TcTS2
                       organism = synthetic construct
SEQUENCE: 5
cgaggcttgc aagttacaca                                                 20

SEQ ID NO: 6           moltype = DNA   length = 20
FEATURE                Location/Qualifiers
source                 1..20
                       mol_type = other DNA
                       note = Downstream primer for amplifying Taxadiene Synthase
                         TcTS2
                       organism = synthetic construct
SEQUENCE: 6
cagggcattt gaaacctcat                                                 20

SEQ ID NO: 7           moltype = DNA   length = 45
FEATURE                Location/Qualifiers
source                 1..45
                       mol_type = other DNA
                       note = Primer P1 for amplifying TcTS1
                       organism = synthetic construct
SEQUENCE: 7
ccgaattcga gctccgtcga catgagcagc agcactggca ctagc                     45

SEQ ID NO: 8           moltype = DNA   length = 45
FEATURE                Location/Qualifiers
source                 1..45
                       mol_type = other DNA
```

-continued

```
                        note = Primer P2 for amplifying TcTS1
                        organism = synthetic construct
SEQUENCE: 8
gtggtgctcg agtgcggccg ctcatacttg aattggatca atata                45

SEQ ID NO: 9            moltype = DNA  length = 47
FEATURE                 Location/Qualifiers
source                  1..47
                        mol_type = other DNA
                        note = Primer P3 for amplifying TcTS2
                        organism = synthetic construct
SEQUENCE: 9
ccgaattcga gctccgtcga catgagcggt agcccgacca agttggc              47

SEQ ID NO: 10           moltype = DNA  length = 49
FEATURE                 Location/Qualifiers
source                  1..49
                        mol_type = other DNA
                        note = Primer P4 for amplifying TcTS2
                        organism = synthetic construct
SEQUENCE: 10
gtggtgctcg agtgcggccg ctcatacttg aatcggttca atgtaaact            49

SEQ ID NO: 11           moltype = DNA  length = 20
FEATURE                 Location/Qualifiers
source                  1..20
                        mol_type = other DNA
                        note = qPCR primer P5 of TcACTIN1
                        organism = synthetic construct
SEQUENCE: 11
gcacggaatt gtttccaact                                            20

SEQ ID NO: 12           moltype = DNA  length = 20
FEATURE                 Location/Qualifiers
source                  1..20
                        mol_type = other DNA
                        note = qPCR primer P6 of TcACTIN1
                        organism = synthetic construct
SEQUENCE: 12
ggcaacatac attgcaggtg                                            20

SEQ ID NO: 13           moltype = DNA  length = 20
FEATURE                 Location/Qualifiers
source                  1..20
                        mol_type = other DNA
                        note = qPCR primer P7 of TcTS1
                        organism = synthetic construct
SEQUENCE: 13
agcactggca ctagcaaggt                                            20

SEQ ID NO: 14           moltype = DNA  length = 20
FEATURE                 Location/Qualifiers
source                  1..20
                        mol_type = other DNA
                        note = qPCR primer P8 of TcTS1
                        organism = synthetic construct
SEQUENCE: 14
ttcacaacca gctcatctgc                                            20
```

TAXADIENE SYNTHASE TcTS2, ENCODING NUCLEOTIDE SEQUENCE AND USE THEREOF

CROSS-REFERENCE TO RELATED APPLICATION

This Application is a continuation of International Application No. PCT/CN2021/097561, filed on Jun. 1, 2021, which claims priority to Chinese Patent Application No. 202010647327.3, filed on Jul. 7, 2020. The disclosures of the aforementioned applications are hereby incorporated by reference in their entireties.

REFERENCE TO AN ELECTRONIC SEQUENCE LISTING

The contents of the electronic sequence listing (CU724SequenceListing. xml; Size: 25, 297 bytes; and Date of Creation: Dec. 29, 2022) is herein incorporated by reference in its entirety.

TECHNICAL FIELD

The present disclosure relates to the technical field of plant genetic engineering, in particular to a taxadiene synthase TcTS2, an encoding nucleotide sequence and use thereof in synthesizing baccatin III or paclitaxel.

BACKGROUND ART

Paclitaxel is a diterpenoid alkaloid, which was first isolated from the bark of *Taxus brevifolia*. It is a widely used anticancer drug, and is widely used in the clinical treatment of various cancers. Cancer is one of the top ten causes of human death. At present, the annual incidence of cancer in the world is still more than 10 million (WHO). Paclitaxel and its preparations are important first-line anticancer drugs. Currently, the main production method of paclitaxel is semi-synthetic method, i.e., firstly the natural precursors baccatin III and 10-deacetylbaccatin III (10-DAB) are extracted, and then paclitaxel is chemically synthesized. (Li et al., 2015; Liu et al., 2016), but the precursor substances used in this method still rely on extraction from plants and are limited by plant or cell resources, which cannot completely solve the supply problem.

Taxadiene synthase (TS) was firstly cloned from *Taxus brevifolia*. Taxadiene synthase (TS) catalyzes the cyclization of Geranylgeranyl Diphosphate (GGPP) to form taxadiene, and taxadiene undergoes a series of functional group reactions to form baccatin III, TS plays an indispensable role in the synthesis of paclitaxel (Wildung et al., 1996).

Taxadiene synthase is the first-step enzyme that catalyzes the formation of taxane skeleton as parent of paclitaxel, and its efficiency of catalyzing cyclization of GGPP is very low as compared with that of other cyclases of gymnosperm. This step is a rate-limiting step of the paclitaxel synthesis pathway, and TS was confirmed to be a slow-rate enzyme. Therefore, it is of great significance to discover paclitaxel biosynthesis genes and the enzymes encoded by them which have higher enzymatic activity.

SUMMARY OF THE INVENTION

In view of this, the object of the present disclosure is to provide a taxadiene synthase TcTS2, which improves the efficiency of catalyzing the cyclization of GGPP, so that the yield of the intermediates taxadiene, baccatin III and the product paclitaxel in the process of synthesizing paclitaxel are greatly improved, thereby significantly reducing the production cost of paclitaxel, and effectively solving the current problem that paclitaxel is expensive and in short supply in the market.

In a first aspect of the disclosure, provided is a taxadiene synthase TcTS2, wherein an amino acid sequence of the taxadiene synthase TcTS2 comprises or consists of:
  a) an amino acid sequence represented by SEQ ID NO: 1; or
  b) a functional homologous sequence having at least 80% sequence similarity with the amino acid sequence represented by SEQ ID NO: 1; or
  c) an amino acid sequence having TcTS2 activity with addition, deletion, or substitution of one or more amino acids in the amino acid sequence represented by SEQ ID NO: 1.

The inventors of the disclosure discovered a new taxadiene synthase gene (named TcTS2) in *Taxus chinensis* var. *maire*, and successfully obtained a encoding protein of this gene (i.e., taxadiene synthase, it is also named as TcTS2 in this disclosure). With research and analysis, the inventors of the disclosure found that the efficiency of TcTS2 for catalyzing the substrate GGPP is significantly higher than that of another type of taxadiene synthase gene TcTS1, and it shows inducible expression pattern under the stress of plant hormone methyl jasmonate (MeJA).

In one implementation of the disclosure, the amino acid sequence of the taxadiene synthase TcTS2 is the amino acid sequence represented by SEQ ID NO: 1, with a total of 758 amino acids.

In one implementation of the disclosure, the amino acid sequence of the taxadiene synthase TcTS2 is a functional homologous sequence having at least 80% sequence similarity with the amino acid sequence represented by SEQ ID NO: 1. The functional homologous sequences with identity includes, but is not limited to, the amino acid sequences having about 80% or more, 82% or more, 84% or more, 85% or more, 88% or more, 90% or more, 92% or more, 93% or more, 94% or more, 95% or more, 96% or more, 97% or more, 98% or more, 99% or more, 99.5% or more, 99.9% or more identity with the amino acid sequence represented by SEQ ID NO: 1.

In one implementation of the disclosure, the amino acid sequence of the taxadiene synthase TcTS2 is an amino acid sequence having TcTS2 activity with addition, deletion, or substitution of one or more (e.g., may be 1, 2, 3, 4, 5, 6, 7, 8, 9, 10, or more) amino acids in the amino acid sequence represented by SEQ ID NO: 1.

In one implementation of the disclosure, the amino acid sequence of the taxadiene synthase TcTS2 is the amino acid sequence represented by SEQ ID NO: 2, with a total of 815 amino acids, which has extra 57 amino acids at the N-terminus as signal peptide sequence as compared with the amino acid sequence represented by SEQ ID NO: 1.

In one implementation of the disclosure, the amino acid sequence of the taxadiene synthase TcTS2 is a functional homologous sequence having at least 80% sequence similarity with the amino acid sequence represented by SEQ ID NO: 2.

In one implementation of the disclosure, the functional homologous sequences with identity includes, but is not limited to, the amino acid sequences having about 80% or more, 82% or more, 84% or more, 85% or more, 88% or more, 90% or more, 92% or more, 93% or more, 94% or more, 95% or more, 96% or more, 97% or more, 98% or more, 99% or more, 99.5% or more, 99.9% or more identity with the amino acid sequence represented by SEQ ID NO: 2.

In one implementation of the disclosure, the amino acid sequence of the taxadiene synthase TcTS2 is an amino acid sequence having TcTS2 activity with addition, deletion, or substitution of one or more (e.g., may be 1, 2, 3, 4, 5, 6, 7, 8, 9, 10, or more) amino acids in the amino acid sequence represented by SEQ ID NO: 2.

The taxadiene synthase TcTS2 of the disclosure significantly improves the efficiency of catalyzing the cyclization of GGPP, reduces the rate-limiting effect, so that the yield of the intermediates taxadiene, baccatin III and the product paclitaxel in the process of synthesizing paclitaxel are greatly improved, thereby significantly reducing the production cost of paclitaxel, and effectively solving the current problem that paclitaxel is expensive and in short supply in the market.

In addition, the expression of taxadiene synthase TcTS2 in plant cells is significantly induced and regulated by methyl jasmonate (MeJA), which is beneficial to the application of synthetic biological technology. The expression of taxadiene synthase TcTS2 may be better regulated by combining the induction of small molecule MeJA and other synthetic biology techniques, which may be used in plant genetic engineering and metabolic engineering to produce paclitaxel and its intermediates in the future.

In a second aspect of the disclosure, provided is a nucleotide sequence encoding the taxadiene synthase TcTS2.

Further, on the basis of the technical solution provided in this disclosure, the nucleotide sequence encoding taxadiene synthase TcTS2 comprises or consists of:
a) a nucleotide sequence represented by SEQ ID NO: 3; or
b) a complementary sequence, a degenerate sequence or a homologous sequence of the nucleotide sequence represented by SEQ ID NO: 3 (preferably with a homology of 70% or more); or
c) a nucleotide sequence that hybridizes to the nucleotide sequence represented by SEQ ID NO: 3 under stringent conditions and is capable of encoding a taxadiene synthase TcTS2; or
d) a cDNA sequence of any one of the nucleotide sequences a)-c).

In one implementation of the disclosure, the nucleotide sequence encoding taxadiene synthase TcTS2 is the nucleotide sequence represented by SEQ ID NO: 3, with a full length of 5138 bases.

In one implementation of the disclosure, the nucleotide sequence encoding taxadiene synthase TcTS2 is a complementary sequence of the nucleotide sequence represented by SEQ ID NO: 3 which is formed according to the principle of base pairing.

In one implementation of the disclosure, the nucleotide sequence encoding taxadiene synthase TcTS2 is a degenerate sequence of the nucleotide sequence represented by SEQ ID NO: 3. Degenerate sequence means that after one or more nucleotide bases of SEQ ID NO: 3 are changed, the encoded amino acid species corresponding to the position having the changed nucleotide base remains unchanged, and will not affect the function of taxadiene synthase TcTS2 gene and the expression level of taxadiene synthase TcTS2.

In one implementation of the disclosure, the nucleotide sequence encoding taxadiene synthase TcTS2 is a homologous sequence of the nucleotide sequence represented by SEQ ID NO: 3.

The homologous nucleotide sequence includes a mutant gene, an allele gene or a derivative that is capable of encoding taxadiene synthase and has enzyme catalytic activity which is formed by addition, and/or substitution, and/or deletion of one or more amino acids in the amino acid sequence represented by SEQ ID NO: 3.

More preferably, the homologous sequence is a polynucleotide having about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more identity with the nucleotide sequence represented by SEQ ID NO: 3.

In one implementation of the disclosure, the nucleotide sequence encoding taxadiene synthase TcTS2 is a nucleotide sequence which is capable of hybridizing with the nucleotide sequence of SEQ ID NO: 3 under stringent conditions and encoding taxadiene synthase TcTS2.

Exemplarily, the "stringent conditions" refer to conditions under which a probe will hybridize to its target sequence to a detectable degree higher than that of the hybridization to other sequences (e.g., at least 2-fold over background). Stringent conditions are sequence-dependent and vary with the environment. By controlling the stringency of hybridization and/or wash conditions, target sequences with 100% complementary to the probe can be identified. Alternatively, stringency conditions can be adjusted to allow some sequence mismatches such that lower degrees of similarity are detected, while such sequence mismatches result in a nucleotide sequence encoding taxadiene synthase TcTS2 without affecting its normal enzymatic activity.

Further, the sequence of the cDNA comprises or consists of:
a) a nucleotide sequence represented by SEQ ID NO: 4; or
b) a degenerate sequence or a homologous sequence of the nucleotide sequence represented by SEQ ID NO: 4; preferably, the homologous sequence is a polynucleotide having about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.5% or more, or 99.9% or more identity with the nucleotide sequence represented by SEQ ID NO: 4.

In one implementation of the disclosure, the nucleotide sequence encoding taxadiene synthase TcTS2 is the cDNA sequence of the nucleotide sequence represented by SEQ ID NO: 4, with a full length of 2448 bases.

In a third aspect of the disclosure, provided is use of the taxadiene synthase TcTS2 or the nucleotide sequence encoding the taxadiene synthase TcTS2 in the synthesis of baccatin III and/or paclitaxel.

Particularly, use of the taxadiene synthase TcTS2 in the synthesis of baccatin III and/or paclitaxel includes the following aspects: (1) the taxadiene synthase TcTS2 provided in this disclosure, or a polypeptide comprising at least part of the amino acid sequence represented by SEQ ID NO: 1, may still have the biological activity of TcTS2 or even have new biological activities after removing or replacing some amino acids, or improve the yield or optimize the protein kinetic characteristics or other properties to be committed to obtain; (2) involved in the biosynthesis of taxadiene; (3) involved in the biosynthesis of paclitaxel and its intermediates (such as baccatin III).

Use of the nucleotide sequence encoding taxadiene synthase TcTS2 in the synthesis of baccatin III or paclitaxel includes the following aspects: (1) the nucleotide sequence or at least part of the nucleotide sequence provided in this disclosure is modified or mutated by means of insertion, deletion, polymerase chain reaction (PCR), error-prone PCR, rejoining of different sequences, directed evolution of different parts of the sequence or homologous sequences from other sources, or mutagenesis by chemical agents, etc.; (2) the cloned gene of the nucleotide sequence or at least part of the nucleotide sequence provided in this disclosure is expressed in an exogenous host through a suitable expression system to obtain the corresponding TcTS2 enzyme or a TcTS2 enzyme with higher biological activity or yield; (3) the gene or gene cluster of the nucleotide sequence or at least part of the nucleotide sequence provided in this disclosure may be used to construct a recombinant plasmid through genetic recombination to obtain a novel biosynthetic pathway, alternatively, a novel biosynthetic pathway may be obtained by insertion, substitution, deletion, or inactivation.

In a fourth aspect of the disclosure, provided are primers for detecting the nucleotide sequence.

There is no specific limitation on the nucleotide sequences for amplifying the PCR product of the nucleotide sequence encoding taxadiene synthase TcTS2, as long as the primers may meet the requirements of specific amplification or specific detection of the nucleotide sequence encoding taxadiene synthase TcTS2.

In a preferred implementation of the disclosure, the primers include an upstream primer and/or a downstream primer; wherein the nucleotide sequence of the upstream primer is represented by SEQ ID NO: 5: 5'-CGAGGCTTGCAAGTTACACA-3'; and/or the nucleotide sequence of the downstream primer is represented by SEQ ID NO: 6: 5'-CAGGGCATTTGAAACCTCAT-3'.

In a fifth aspect of the disclosure, provided is a vector into which the nucleotide sequence is introduced.

The type of the vector is not specifically limited, and it may be a vector commonly used in the art. Examples of the vector include, but are not limited to, pET28b, pIJ702, pUCP19, pYMB03 or pHT43; preferably pET28b.

In a sixth aspect of the disclosure, provided is a host cell into which the nucleotide sequence or the vector is introduced.

Further, the host cells include plant cells and/or microbial cells.

Further, the plant cells include but are not limited to *Taxus* cells, tobacco cells, *Pseudotaxus chienii* cells, and *Artemisia carvifolia* cells.

Further, the microbial cells include, but are not limited to *Streptomyces, Pseudomonas, Bacillus*, yeast cells, and *Escherichia coli*.

Further, in vivo and in vitro methods for introducing the nucleotide sequence encoding taxadiene synthase TcTS2, or the recombinant plasmid, or the expression vector into a host cell include but are not limited to: electroporation, polyethylene glycol (PEG) transformation, lipofection, heat shock, calcium phosphate precipitation, virus mediation and microinjection.

In a seventh aspect of the disclosure, provided is a method for expressing taxadiene synthase TcTS2 in a plant, which comprises transforming the nucleotide sequence, or the vector, or the host cell into a plant to obtain the taxadiene synthase TcTS2.

Further, the plants include but are not limited to: *Taxus, Pseudotaxus chienii*, tobacco, and *Artemisia carvifolia*.

Further, the plant body also includes plant parts such as explants, including but not limited to, cuttings, tissue cultures, cell suspensions, and calli.

Further, the plant is more preferably *Taxus* and/or tobacco.

In an eighth aspect of the disclosure, provided is a method for producing paclitaxel and its intermediates, which includes expressing the taxadiene synthase TcTS2 in a plant.

Further, the method includes: transforming the nucleotide sequence, or the vector, or the host cell into a plant to express the taxadiene synthase TcTS2 to obtain paclitaxel and its intermediates.

This disclosure adopts the above-mentioned technical solutions to have the following beneficial effects:

(1) The disclosure provides a taxadiene synthase TcTS2, which improves the efficiency of catalyzing the cyclization of GGPP, so that the yield of the intermediates taxadiene, baccatin III and the product paclitaxel in the process of synthesizing paclitaxel are greatly improved, thereby significantly reducing the production cost of paclitaxel, and effectively solving the current problem that paclitaxel is expensive and in short supply in the market.

(2) The expression of taxadiene synthase TcTS2 in plant cells is significantly induced and regulated by methyl jasmonate (MeJA), by combining the induction of small molecule MeJA and other synthetic biology techniques, which may be used in plant genetic engineering and metabolic engineering modification to produce paclitaxel and its intermediates and other aspects in the future.

(3) The nucleotide sequence encoding taxadiene synthase TcTS2 provided in this disclosure provides new gene resource for improving the yield of paclitaxel, and the nucleotide sequence and TcTS2 may be used for modifying chassis hosts by plant genetic engineering and metabolic engineering strategies to produce paclitaxel and the intermediates thereof etc., thereby having significant economic and social value.

DETAILED DESCRIPTION OF THE EMBODIMENTS

Figure 1:
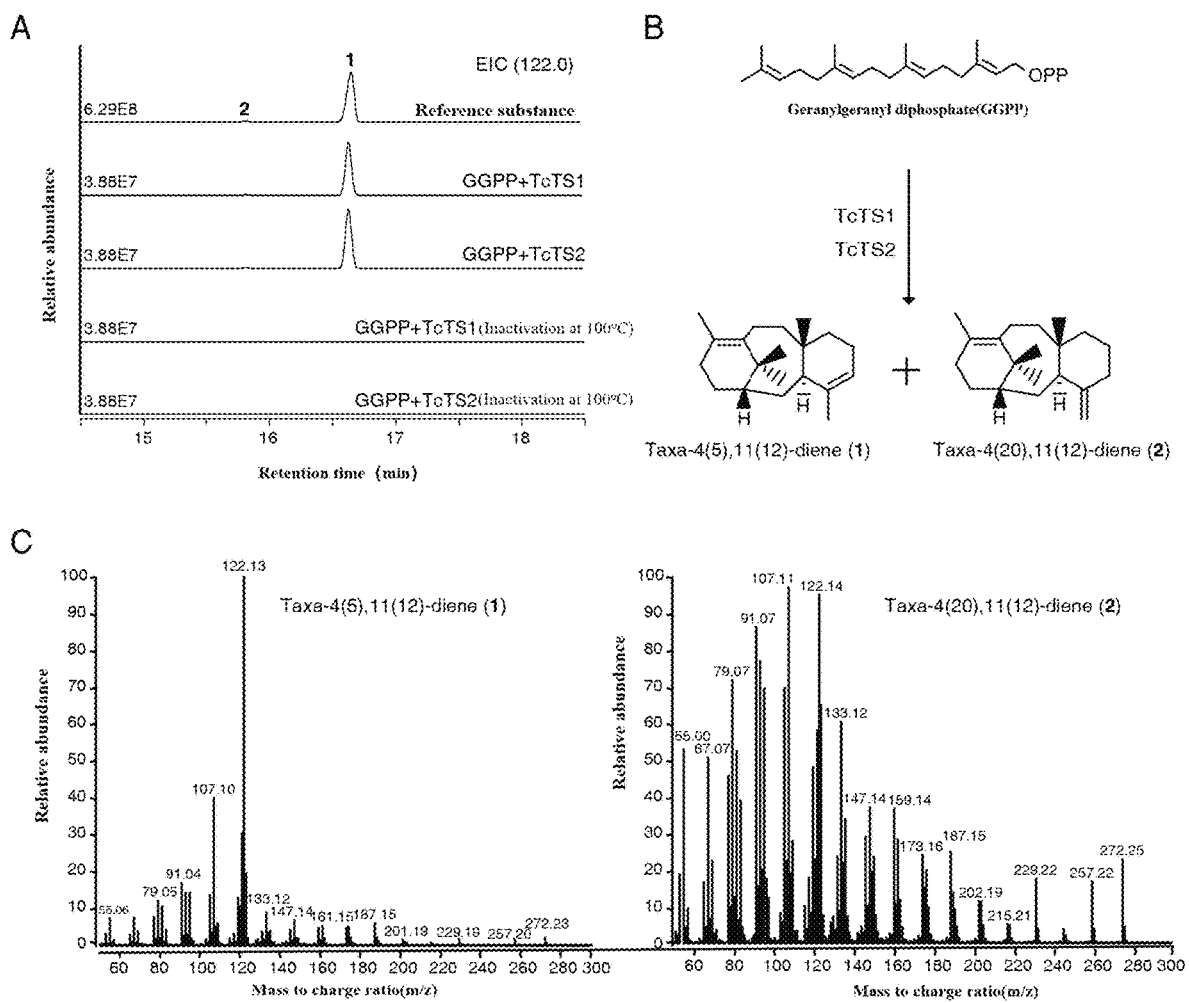
FIG. 1 shows an analysis of the in vitro biochemical activity of TcTSs. Particularly, A is a chromatogram of GC-MS detection of TcTSs enzymatic reaction product, and the characteristic ion m/z 122 of taxadiene is extracted; B is a schematic diagram of TcTSs-catalyzed GGPP cyclization reaction to generate taxadiene; C is a mass spectrum of TcTSs enzymatic reaction product.

In this disclosure, the term "TcTS2" may refer to taxadiene synthase, or taxadiene synthase gene, or a nucleotide sequence encoding taxadiene synthase, and the specific meaning can be determined according to the context.

In this disclosure, the term "gene" is defined as a genetic unit (usually represented by a DNA sequence) that occupies a specific location in a chromosome and contains genetic instructions that contribute to an underlying phenotypic character or trait in a plant.

In this disclosure, the term "nucleotide" is used in its ordinary meaning as understood by those skilled in the art.

In this disclosure, the term "amino acid" refers to any amino acid (both standard and non-standard amino acids), including but not limited to: alpha-amino acids, beta-amino acids, gamma-amino acids, and delta-amino acids. Examples of suitable amino acids include, but are not limited to: alanine, asparagine, aspartic acid, cysteine, glutamic acid, glutamine, glycine, proline, serine, tyrosine, arginine, histidine, isoleucine, leucine, lysine, methionine, phenylalanine, threonine, tryptophan and valine.

Unless otherwise defined, all scientific and technical terms used in this disclosure have the same meaning as commonly understood by one of ordinary skill in the art to which this disclosure relates.

The technical solutions in the embodiments of the disclosure will be clearly and completely described below with reference to the accompanying drawings in the embodiments of the disclosure. Obviously, the described embodiments are only a part of the embodiments of the present disclosure, but not all of the embodiments. Based on the embodiments in the disclosure, all other embodiments obtained by those of ordinary skill in the art without creative efforts shall fall within the protection scope of the disclosure.

The materials, reagents, etc. used in the following examples can be obtained from commercial sources unless otherwise specified.

The disclosure will be described in detail below with reference to specific embodiments, which are used to understand rather than limit the disclosure.

Embodiment 1: Cloning, Expression and Purification of Taxadiene Synthase TcTSs Genes 1. Cloning and Sequence Analysis of Taxadiene Synthase TcTSs Gene Taxadiene synthase TbTS from *Taxus brevifolia* (GeneBank NO. U48796) with a known function was used as a target sequence to search in the genome of *Taxus chinensis* var. *mairei*, and two taxadiene synthase genes were found and named as TcTS1 and TcTS2, respectively. Particularly, after sequence comparison and analysis, it was found that: the amino acid sequence of the reading frame of TcTS1 is 98% homologous to TbTS, while TcTS2 is a newly discovered taxadiene synthase gene, and the genomic DNA sequence of TcTS2 is represented by SEQ ID NO: 3 and has 42% similarity with TbTS nucleotide. The reading frame nucleotide sequence and amino acid sequence of the TcTS2 are represented by SEQ ID NO: 4 and SEQ ID NO: 1 respectively, and the similarity of nucleotide and the homology of amino acid sequence with TbTS are both 79%.

Previous studies have confirmed that, when taxadiene synthase is heterologously expressed in the *E. coli* system, its 5' terminal signal peptide sequence will affect its catalytic activity (Wildung et al., 1996). Therefore, the applicant selected three online softwares (Plant-Ploc, ChloroP and TargetP) to predict the positions of TcTS1 and TcTS2 chloroplast transit peptides, and the results showed that: the 58 amino acids at the 5' end of TcTS1 are signal peptide sequences, and the 57 amino acids at the 5' end of TcTS2 are signal peptide sequences.

For subsequent biochemical function identification, based on the nucleotide sequences of the TcTS1 and TcTS2 genes, the applicant designed primers P1 and P2, primers P3 and P4 for respectively amplifying the TcTS1 and TcTS2 genes according to the sequences after deleting the position of the signal peptide. The primers comprise part of the sequence of prokaryotic expression vector pET28b, and a vector whose N-terminus is fused and expressed with 6 histidines was constructed for the convenience of subsequent purification. The sequence of the first 40 amino acids at the N-terminal encoded by SEQ ID No. 3 is the sequence on the pET28b vector.

Using the cDNA of *Taxus chinensis* var. *mairei* cell line 104 as the template, PCR was used to amplify the TcTS1 and TcTS2 genes. After the PCR product was recovered by gel cutting, it was recombined with the linear pET28b vector double-digested by Sal I and Not I. Hieff Clone™ one-step cloning kit (YEASEN, China) was used for cloning and sequencing, and the positive recombinant plasmids were named as pET28b-TcTS1 and pET28b-TcTS2, respectively.

Among the primers used, P1 and P2 were used to amplify TcTS1, and P3 and P4 were used to amplify TcTS2, particularly the primer sequences are as follows:

```
P1:
                                 (SEQ ID NO: 7)
5'-CCGAATTCGAGCTCCGTCGACATGAGCA

GCAGCACTGGCACTAGC-3'
(Cleavage site of Sal I restriction
enzyme is underlined)

P2:
                                 (SEQ ID NO: 8)
5'-GTGGTGCTCGAGTGCGGCCGCTCATACT

TGAATTGGATCAATATA-3'
(Cleavage site of Not I restriction
enzyme is underlined)

P3:
                                 (SEQ ID NO: 9)
5'-CCGAATTCGAGCTCCGTCGACATGAGCG

GTAGCCCGACCAAGTTGGC-3'
(Cleavage site of Sal I restriction
enzyme is underlined)

P4:
                                 (SEQ ID NO: 10)
5'-GTGGTGCTCGAGTGCGGCCGCTCATACT

TGAATCGGTTCAATGTAAACT-3'.
(Cleavage site of Not I restriction
enzyme is underlined)
```

2. Heterologous Expression and Purification of Taxadiene Synthase TcTSs

Induced expression of TcTSs-His6 fusion protein: the constructed fusion expression vectors pET28b-TcTS1 and pET28b-TcTS2 were respectively transferred into *E. coli* BL21 (DE3) to obtain BL21 (DE3)/pET28b-TcTS1 and BL21 (DE3)/pET28b-TcTS2 transgenic strain; positive single clones were picked and inoculated in LB medium (containing 50 µg/mL of kanamycin), incubating overnight at 37° C.; the overnight culture was taken to add into 300 mL of fresh LB medium (containing 50 µg/mL of kanamycin) at a ratio of 1:100 to expand and culture at 37° C. to an OD600 value of 0.4-0.6; IPTG (isopropyl thiogalactoside) was added to a final concentration of 1.0 mmol/L for induced expression at 16° C., 160 rpm for 12 h; then centrifuging at 12,000 rpm to collect the strains for purification.

The TcTSs-His6 fusion protein was purified according to HisPur Ni NTA Resin and desalting ultrafiltration tube method of Thermo Scientific Company in the United States: the collected strains were resuspended in 20 ml of lysis buffer (50 mM sodium phosphate, pH 8.0, 300 mM NaCl, 10 mM imidazole), ultrasonic degradation method was used to break the wall, centrifuging at 4° C., 4,000 g for 20 min, the supernatant was loaded into a 1.5 ml HisPur Ni-NTA resin packing column (Thermo Scientific, USA), after removing impurities elution buffer solution (50 mM sodium phosphate, 300 mM NaCl, 50 mM imidazole) was used for eluting.

The purified recombinant TcTSs-His6 was desalted by using a 30 kDa ultrafiltration tube, and stored in enzyme reaction buffer (25 mM HEPES, pH8.5, 10% glycerol, 5 mM DTT, 5 mM sodium ascorbate, 5 mM sodium metabisulfite and 1 mM $MgCl_2$). The content and purity of the recombinant protein TcTSs-His6 were detected by using BCA protein detection kit (Beyotime, China), bovine serum albumin (BSA) standard and SDS-PAGE gel electrophoresis, respectively.

The results show that: TcTS1-His6 fusion protein and TcTS2-His6 fusion protein are both soluble expression, and the purity of purified protein is as high as 98%, and the concentrations are 3.4 µg/µL and 1.8 µg/µL, respectively.

Embodiment 2: Biochemical Function Analysis of Taxadiene Synthase TcTSs

1. In Vitro Activity of TcTSs-His6

The in vitro enzymatic reaction system was 500 µL, containing 100 µg purified protein, 100 µM GGPP (Sigma-Aldrich) and enzyme reaction buffer (25 mM, pH 8.5, 10% glycerol, 5 mM DTT, 5 mM ascorbate, 5 mM sodium metabisulfite and 1 mM $MgCl_2$), the reaction mixture was covered with 500 µL of pentane (Macklin, GC-MS grade) and reacted in a 32° C. water bath for 2 h, vortexing for 2 min, centrifuging at 5000 rpm for 10 min; the pentane layer was taken out, putting into 2 mL of the sample, concentrating at low temperature by using a nitrogen blower; the product was analyzed by gas chromatography mass spectrometry (GC-MS) instrument.

The control group was the reaction product of purified recombinant protein TcTSs-His6 after being boiled at 100° C. for 10 min. The GC-MS instrument was Agilent 7890B/7000C (Agilent Technologies, Waldbronn, USA), mass spectrometry detector parameters: 70 eV, helium flow rate 1.2 mL/min, chromatographic column Agilent HP-5 MS (5% phenylmethyl silica, 30 m×250 µm inner diameter, 0.25 µm film thickness), the injection volume is 1-5 µL; the temperature program of the column oven is as follows: 45° C. for 1 min, then 10° C./min gradient increase to 250° C., and remaining at 250° C. for 5 min. The temperature of the injection port was 250° C.; the mass-to-charge ratio (m/z) of the scan was 40-350, and the qualitative analysis of the enzymatic product was carried out with the taxadiene standard as the reference.

The results of in vitro biochemical function analysis are shown in FIG. 1. The results show that: both TcTS1 and TcTS2 can catalyze the substrate GGPP to generate the main products taxa-4 (5), 11 (12)-diene (accounting for 94%) and the secondary products taxa-4 (20), 11 (12)-diene (accounting for 4%), showing the same taxadiene synthase activity. C of FIG. 1 shows a mass spectrum of the product of the enzymatic reaction of TcTSs, which is used to characterize the enzymatic product.

2. Comparison of Kinetic Constants of TcTSs-His6

Kinetic parameter detection: standard enzymatic reaction with a total volume of 100 µL, containing enzyme reaction buffer (25 mM, pH 8.5, 10% glycerol, 5 mM DTT, 5 mM ascorbate, 5 mM sodium metabisulfite and 1 mM $MgCl_2$), 34 µg (TcTS1-His6) or 18 µg (TcTS2-His6) recombinant protein, and 7 different concentrations of GGPP (0.2 µM, 0.5 µM, 1 µM, 2.5 µM, 5 µM, 10 µM, 25 µM, 50 µM) mixed with [13H]-GGPP substrate (American Radiolabeled Chemicals, Inc, 30 Ci/mM).

Labeled [1-3H]-GGPP was diluted 400-fold with unlabeled GGPP (Sigma, 1 mg/mL). The reaction mixture was reacted at 32° C. for 30 min, then quenching with 100 µL of stop buffer (containing IM EDTA and 4M NaOH) for 10 min; the reaction mixture was extracted with 800 µL of n-hexane (vortexing for 2 min, centrifuging at 12,000 rpm for 10 min); 400 µL of n-hexane extract was taken to add into 2 mL of liquid scintillation cocktail to mix well. The total radioactivity of the reaction products was determined by using a liquid scintillation counter (Tri-Carb 2910TR, Perkin Elmer). Kinetic constants were calculated by nonlinear regression fitting of Michaelis-Menten equation through Origin 8.6 software.

The kinetic constant results show that: the $K_a$ of TcTS1-His6 and TcTS2-His6 are 5.5±1.6 and 8.6±1.5 (pM/µg/min) respectively, while the $K_{cat}$ values of TcTS1-His6 and TcTS2-His6 are 0.00292 (1/s) and 0.00901 (1/s) respectively. It can be seen from their $K_a$ and $K_{cat}$ values, although TcTS1-His6 binds GGPP 1.6 times more strongly than TcTS2-His6, the catalytic efficiency of TcTS2-His6 is 3 times more than that of TcTS1-His6 ($K_{cat}$ value). The kinetic constant results show that: the enzyme catalytic efficiency of TcTS2 is significantly better than that of TcTS1, and the application prospect of synthetic biology is also significantly better than that of TcTS1.

Embodiment 3: Correlation Analysis of Taxadiene Synthase TcTSs Gene Expression and paclitaxel under Methyl Jasmonate Stress 1. Experiments on the Treatment of *Taxus chinensis* var. *mairei* Cell Line 211 with Methyl Jasmonate

*Taxus chinensis* var. *mairei* cell line 211 were divided into two groups: the experimental group (MeJA+) was soaked with 100 µM methyl jasmonate; the control group (MeJA−) was soaked with 0.05% ethanol solution. The experiments of the two groups were carried out at the same time, and the samples were collected after 0 h, 2 h, 3 h and 4 h respectively, for the analysis of the expression pattern of TcTSs gene and the content of baccatin III and paclitaxel, with three biological replicates.

2. Analysis on the Content Changes of Baccatin III and Paclitaxel for Different Treatment Times of MeJA The metabolites were extracted by the modified Wolfender method. The specific steps include: weighing 100 mg of lyophilized cell powder to place it in a 2 ml centrifuge tube, adding 1.5 ml of extraction buffer (methanol:water=80:20, v/v) and vortexing to suspend it, containing 500 ng/ml dexamethasone as the internal standard, after ultrasonic extraction for 30 min, centrifuging at 14,000 g for 15 min; the supernatant was centrifuged and dried in a vacuum concentrator (LABCONCO), and finally the sample was resuspended in 200 μL methanol solvent (80:20, v/v) for LCMS analysis. Samples were analyzed by LC-MS by using an ACQUITY UPLC I-Class/AB SCIEX (Waters) instrument.

The separation column was Waters (2.1×50 mm; ACQUITY UPLC™ Waters XselectHSS T3); the injection volume was 10 μL, and the flow rate was 0.2 mL/min.

The mobile phase composition: A was 0.1% formic acid methanol; B was 0.1% formic acid water.

The LC separation procedure was as follows: equilibrating with 40% A for 2 min, followed by gradient elution for 10 min to 100% B, maintaining for 2 min, and then returning to 40% A equilibration for 1 min. ESI ion source, positive ion mode. Data acquisition and processing were performed on AB SCIEXAnalyst 1.6.3 software (Applied Biosystems).

Figure 2:
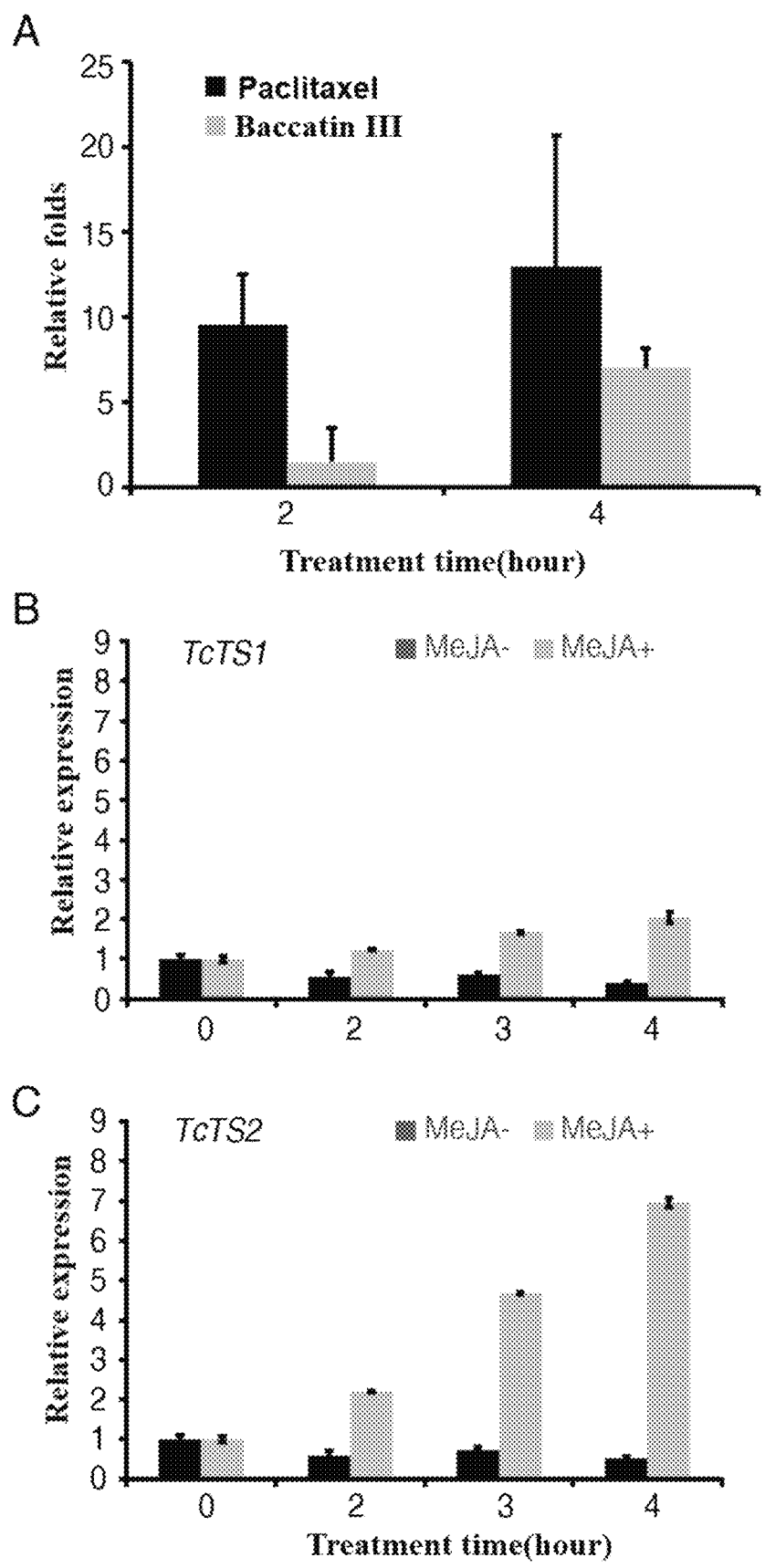
FIG. 2 shows changes in metabolite content and the expression pattern of TcTSs genes under MeJA stress. Particularly, A is a relative change of the yields of baccatin III and paclitaxel under MeJA stress; B is an expression pattern of TcTS1 gene under MeJA stress; C is an expression pattern of TcTS2 gene under MeJA stress; MeJA+ indicates 100 µM MeJA treatment group; MeJA-indicates a solvent control group.

The quantitative analysis of metabolites in A of FIG. 2 shows that: the treatment of 100 μM MeJA significantly promotes the accumulation of paclitaxel and baccatin III, and after treating with MeJA for 2 h, the increased folds of paclitaxel and baccatin III are 9.53 and 1.48 times respectively, as compared to the control group; after treating with MeJA for 4 h, the increase folds of paclitaxel and baccatin III are 12.91 and 7.01 times respectively.

3. Analysis on Expression Pattern of TcTS2 Gene for Different Treatment Times of MeJA EASYspin Plant Total RNA Extraction Kit (Aidlab, Beijing) was used to extract and collect the total RNA of the samples with different treatment times. 1 μg of total RNA of different samples was respectively taken for the synthesis of the first-strand cDNA, using it as the template for real-time fluorescence quantitative PCR. Kit Hifair® III 1st Strand cDNA Synthesis (YEASEN, China) and qPCR fluorescent dye kit Hieff® qPCR SYBR® Green Master Mix (Low Rox Plus) (commercial reagents, purchased from YEASEN, China) were used for the first-strand cDNA synthesis. qPCR experiments were performed on the QuantStudio™ 3 system with 2 technical replicates and 3 biological replicates. Actin1 (TcACTIN1) gene of *Taxus chinensis* var. *mairei* was used as an internal reference gene, and the relative expression of TcTSs genes was calculated by using the $2^{-\Delta\Delta Ct}$ method.

Gene-specific primers for qPCR are as follows:

P5:
(SEQ ID NO: 11)
5'-GCACGGAATTGTTTCCAACT-3'
(TcACTIN1)

P6:
(SEQ ID NO: 12)
5'-GGCAACATACATTGCAGGTG-3'
(TcACTIN1)

P7:
(SEQ ID NO: 13)
5'-AGCACTGGCACTAGCAAGGT-3'
(TcTS1)

P8:
(SEQ ID NO: 14)
5'-TTCACAACCAGCTCATCTGC-3'
(TcTS1)

-continued

P9:
(SEQ ID NO: 5)
5'-CGAGGCTTGCAAGTTACACA-3'
(TcTS2)

P10:
(SEQ ID NO: 6)
5'-CAGGGCATTTGAAACCTCAT-3'.
(TcTS2)

The qPCR results of B and C of FIG. 2 show that: the expressions of TcTS1 and TcTS2 are both up-regulated under MeJA stress, but showing different expression patterns. As for different MeJA treatment times, the up-regulation of TcTS1 tends to be stable, showing a constitutive expression pattern; on the contrary, the up-regulation of TcTS2 is significant, the most significant induction time node is 4 h, and the induction fold is 7 relative to 0 h, showing an inducible expression pattern.

Combined with the results of metabolite quantitative analysis and gene expression pattern analysis, under MeJA stress, the expression of TcTS2 is significantly up-regulated, and the yield of paclitaxel and baccatin III is significantly increased. The above results indicate that: the expression of TcTS2 in plant cells is significantly regulated by the phytohormone methyl jasmonate (MeJA), which promotes the synthesis of baccatin III and paclitaxel. The inducible expression of TcTS2 gene is more conducive to the application of synthetic biological technology, and the synthetic application prospect is significantly better than that of TcTS1.

To sum up, the novel taxadiene synthase gene TcTS2 provided in this disclosure is significantly different from another type of taxadiene synthase gene TcTS1, and the expressed proteins are also significantly different, the enzyme catalytic efficiency of TcTS2 is significantly higher, and inducible expression is presented under MeJA stress, which significantly promotes the synthesis of baccatin III and paclitaxel.

Embodiment 4: Comparison of the Synthesis of Taxadiene by TcTS2 and TbTS in Engineered Strains 1. Construction of Engineered *Escherichia coli* Strain Based on reported techniques (Bian et al., 2017), TcTS2 and TbTS were used to construct taxadiene-producing engineered strains *E. coli* TcTS2 and *E. coli* TbTS, respectively.

2. Comparison of Synthesis of Taxadiene by the above Two Engineered Strains (1) Comparison of growth potential of the two engineered strains: engineered strains *E. coli* TbTS and *E. coli* TcTS2 were respectively inoculated in 30 ml of LB-liquid medium containing ampicillin (100 mg/L), kanamycin (50 mg/L) and chloramphenicol (34 mg/L), growing at 37° C. with shaking overnight; the solution of each strain was taken for low-speed centrifugation to remove the supernatant, resuspending with the induction medium to OD600=0.3, adding IPTG for induction (the final concentration is 0.1 mM); 200 μL of the induced culture strain solution was taken to add to a 96-well plate (3 parallel samples), culturing and shaking at 28° C. by a multi-function microplate reader capable of continuously culturing, and automatically detecting OD600 every 15 min; after co-culturing for 40 h, a growth curve is plotted based on the arithmetic mean values, as shown in FIG. 3.

Figure 3:
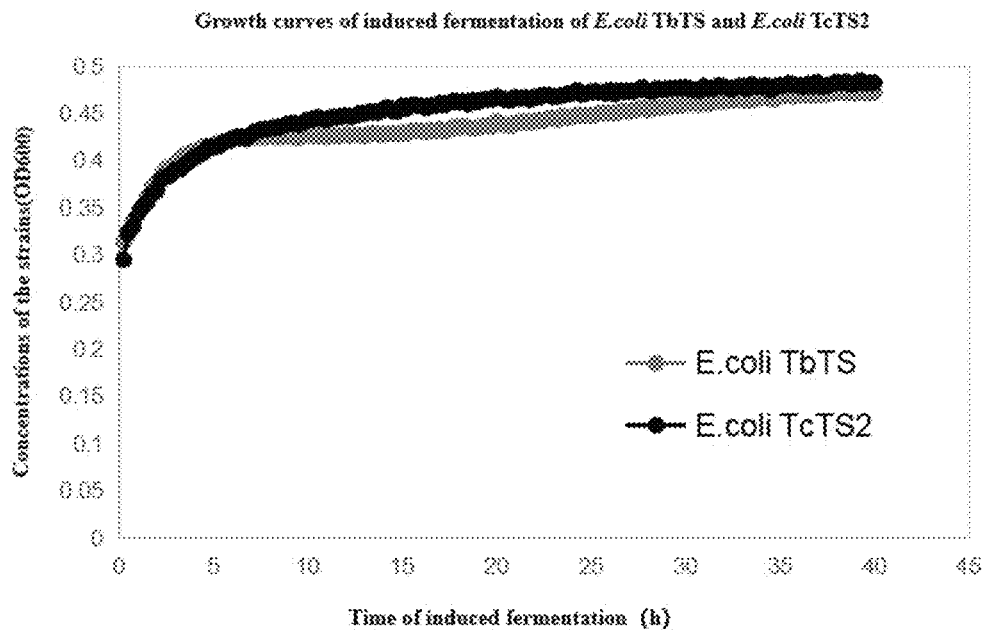
FIG. 3 shows the growth curves of induced fermentation of the engineered strains *E. coli* TbTS and *E. coli* TcTS2 in Embodiment 4.

The results in FIG. 3 show that: the growth trends of *E. coli* TbTS and *E. coli* TcTS2 strains are basically the same.

Figure 4:
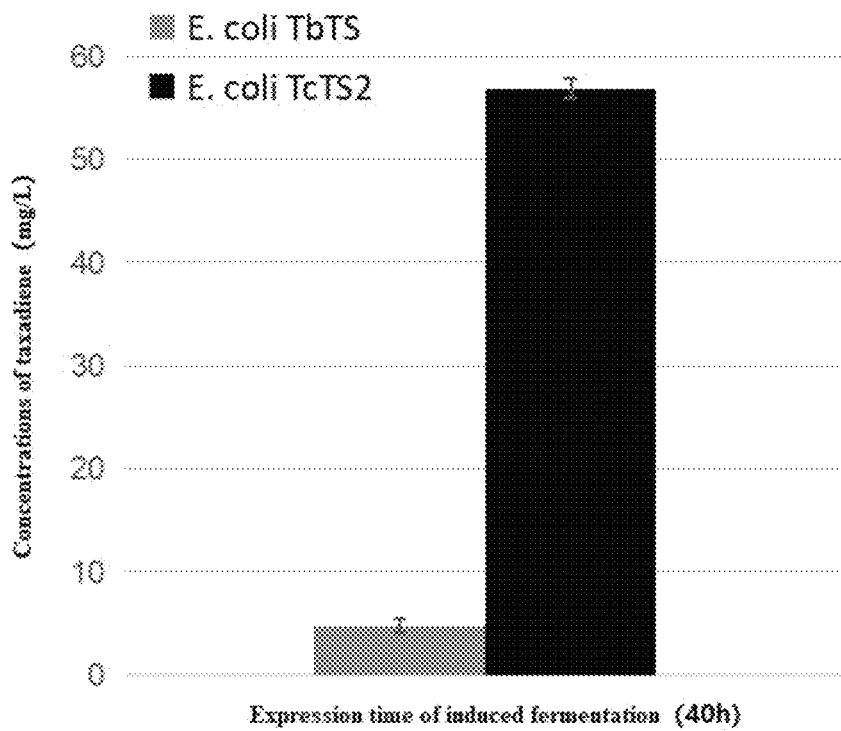
FIG. 4 shows the comparison of the yields of taxadiene products synthesized by the engineered strains *E. coli* TbTS and *E. coli* TcTS2 in Embodiment 4.

The detection of the synthetic taxadiene product of two kinds of engineered strains: the fermentation product of the above engineered strains is respectively detected by GC-MS, and the GC-MS detection method is the same as that in embodiment 2; the target peak of its chromatogram is integrated, and the concentration is converted by area integration, the results are shown in FIG. 4. It can be seen that, the yield of the target product expressed by *E. coli* TcTS2 is 12 times higher than that of *E. coli* TbTS.

The comprehensive results show that: the ability of TcTS2 to synthesize taxadiene is significantly better than that of TbTS, and the yield may be greatly improved by using TcTS2 to synthesize taxadiene.

Reference: Bian, G. et al. Production of taxadiene by engineering of mevalonate pathway in *Escherichia coli* and endophytic fungus *Alternaria alternata* TPF6. Biotechnol. J. 12 (2017).

The above examples are only preferred embodiments of the disclosure, and are not intended to limit the disclosure. Any modifications, equivalent replacements, etc. made within the spirit and principles of the disclosure shall be encompassed in the protection scope of the disclosure.

What is claimed is:

1. A recombinant DNA vector comprising a heterologous nucleic acid sequence, wherein the nucleic acid sequence encodes a protein named TcTS2 (*Taxus chinensis* Taxadiene synthase 2) comprising SEQ ID NO: 1 or SEQ ID NO: 2, and wherein the vector is capable of conferring taxadiene synthase activity when transformed into a host cell.

2. The recombinant DNA vector of claim 1, wherein the nucleic acid sequence comprises SEQ ID NO: 3 or SEQ ID NO: 4.

3. A transgenic microbial cell having taxadiene synthase activity, wherein the activity is conferred by a transgene comprising a nucleic acid sequence encoding a TcTS2 protein comprising SEQ ID NO: 1.

4. The transgenic microbial cell of claim 3, wherein the microbial cell is *Streptomyces, Pseudomonas, Bacillus*, a yeast cell, or *Escherichia coli*.

5. A transgenic plant, plant part, or plant cell having taxadiene synthase activity, wherein the activity is conferred by a transgene comprising a nucleic acid sequence encoding a TcTS2 protein comprising SEQ ID NO: 2.

6. The transgenic plant, plant part, or plant cell of claim 5, wherein the plant, plant part, or plant cell is *Taxus*, tobacco, *Pseudotaxus chienii*, or *Artemisia carvifolia*.

7. A method for producing a transgenic plant, plant part, or plant cell having taxadiene synthase activity, the method comprising:
    transforming a plant, plant part, or plant cell with an isolated, recombinant, or synthetic polynucleotide comprising: a nucleic acid sequence encoding a protein comprising SEQ ID NO: 2; and
    selecting a plant comprising the polynucleotide and having taxadiene synthase activity.

8. The method for producing a transgenic plant, plant part, or plant cell of claim 7, wherein the transforming comprises transforming a recombinant DNA vector into a plant, plant part, or plant cell, wherein the recombinant DNA vector comprises a heterologous nucleic acid sequence encoding a TcTS2 protein comprising SEQ ID NO: 2.

9. The method for producing a transgenic plant, plant part, or plant cell of claim 7, wherein the plant, plant part, or plant cell is *Taxus*, tobacco, *Pseudotaxus chienii*, or *Artemisia carvifolia*.

10. A method for synthesis of baccatin III and/or paclitaxel, the method comprising: transforming a nucleic acid sequence encoding a TcTS2 protein comprising SEQ ID NO: 1 or SEQ ID NO: 2 into a host cell, wherein the TcTS2 protein is expressed, and isolating baccatin III and/or paclitaxel.

11. The method for synthesis of baccatin III and/or paclitaxel of claim 10, wherein the nucleic acid sequence encoding a TcTS2 protein is contained within a recombinant DNA vector.

12. The method for synthesis of baccatin III and/or paclitaxel of claim 10, wherein the host cell is a plant cell or a microbial cell.

13. The method for synthesis of baccatin III and/or paclitaxel of claim 12, wherein the microbial cell is *Streptomyces, Pseudomonas, Bacillus*, a yeast cell, or *Escherichia coli*.

14. A method for synthesis of baccatin III and/or paclitaxel, the method comprising: obtaining the transgenic microbial cell of claim 3, and isolating baccatin III and/or paclitaxel.

15. A method for producing paclitaxel and an intermediate thereof, the method comprising: obtaining the transgenic plant, plant part, or plant cell of claim 5, and isolating paclitaxel and its intermediates.

16. A method for producing paclitaxel and an intermediate thereof, the method comprising: transforming the nucleotide sequence encoding a TcTS2 protein comprising SEQ ID NO: 2 into a plant, plant part, or plant cell to express said protein, and isolating paclitaxel and its intermediates.

17. The method for producing paclitaxel and an intermediate thereof of claim 16, wherein the nucleotide sequence encoding a TcTS2 protein is contained within a recombinant DNA vector.

* * * * *